(12) United States Patent  
Ochs

(10) Patent No.: US 8,152,508 B2  
(45) Date of Patent: Apr. 10, 2012

(54) APPARATUS FOR MANUFACTURE OF SINGLE-USE DENTAL FLOSS HOLDERS

(75) Inventor: Harold D. Ochs, Flemington, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 71 days.

(21) Appl. No.: 12/789,587

(22) Filed: May 28, 2010

(65) Prior Publication Data

US 2011/0293772 A1    Dec. 1, 2011

(51) Int. Cl.
B29C 45/16 (2006.01)
(52) U.S. Cl. .................. 425/116; 425/127; 425/129.1
(58) Field of Classification Search .................. 425/110, 425/116, 127, 117, 129.1
See application file for complete search history.

(56) References Cited

U.S. PATENT DOCUMENTS

| | | |
|---|---|---|
| 778,388 A | 12/1904 | Warren |
| 1,111,144 A | 9/1914 | Epstein et al. |
| 1,874,433 A | 8/1932 | Briggs |
| 2,187,899 A | 1/1940 | Henne |
| 2,354,454 A | 7/1944 | Geffner |
| 2,872,929 A | 2/1959 | Rice |
| 3,182,345 A | 5/1965 | Smith |
| 3,631,869 A | 1/1972 | Espinosa |
| 3,892,249 A | 7/1975 | Jones et al. |
| 3,926,201 A | 12/1975 | Katz |
| 3,927,686 A | 12/1975 | Zambito |
| 4,006,750 A | 2/1977 | Chodorow |
| 4,026,308 A | 5/1977 | Krivit |
| 4,051,857 A | 10/1977 | Zambito |
| 4,192,330 A | 3/1980 | Johnson |
| 4,729,392 A * | 3/1988 | Tenny ............................ 132/323 |
| 4,942,892 A | 7/1990 | Hill |
| 5,010,906 A | 4/1991 | Preciutti |
| 5,056,540 A | 10/1991 | Page |
| 5,125,424 A | 6/1992 | Eisen |
| 5,127,415 A | 7/1992 | Preciutti |
| 5,165,913 A | 11/1992 | Hill et al. |
| 5,170,809 A | 12/1992 | Imai et al. |
| 5,261,430 A | 11/1993 | Mochel |
| 5,388,600 A | 2/1995 | Hart |
| 5,392,794 A * | 2/1995 | Striebel ........................ 132/324 |

(Continued)

FOREIGN PATENT DOCUMENTS

DE    198708369 U    10/1987

(Continued)

*Primary Examiner* — Timothy Heitbrink

(57) ABSTRACT

The invention concerns a mold for forming a single-use floss holder containing a length of dental floss having a wax composition applied thereto, the mold including a first part having a first cavity disposed therein, the first cavity defined by a bottom base surface and a peripheral sidewall, and including a base portion, first and second spaced-apart portions having proximal and distal sections and extending from the base portion, and a second part having a second cavity disposed therein, the second cavity defined by a bottom base surface and a peripheral sidewall, and including a base portion, first and second spaced-apart portions having proximal and distal sections and extending from the base portion and terminating in the distal section; and a groove having an aspect ratio of about 10:1 or greater and having first and second terminal sections and a mid-section, the groove extending an entire width of the second part, where the first and second terminal sections of the groove traverse and are coincident with the distal section of the first and second spaced-apart portions of the second cavity, respectively.

11 Claims, 4 Drawing Sheets

U.S. PATENT DOCUMENTS

| | | | |
|---|---|---|---|
| 5,411,041 A | 5/1995 | Ritter | |
| 5,483,982 A | 1/1996 | Bennett et al. | |
| 5,538,023 A * | 7/1996 | Oczkowski et al. | 132/323 |
| 5,570,709 A | 11/1996 | Haddad et al. | |
| 5,579,786 A | 12/1996 | Wolk et al. | |
| 5,692,531 A | 12/1997 | Chodorow | |
| 5,738,124 A | 4/1998 | Cervato | |
| 5,819,769 A | 10/1998 | Gutierrez | |
| 5,860,434 A * | 1/1999 | Sines et al. | 132/323 |
| 6,018,838 A | 2/2000 | Nowack | |
| 6,065,479 A * | 5/2000 | Chodorow | 132/323 |
| 6,085,760 A * | 7/2000 | Chodorow | 132/323 |
| 6,457,201 B1 | 10/2002 | Sham | |
| D497,222 S | 10/2004 | Ochs et al. | |
| 7,059,334 B2 | 6/2006 | Dougan et al. | |
| 7,171,971 B2 | 2/2007 | Ochs et al. | |
| 7,174,904 B2 | 2/2007 | Ochs et al. | |
| 7,325,554 B2 | 2/2008 | Ochs | |
| 7,370,658 B2 * | 5/2008 | Chodorow et al. | 132/323 |
| 2003/0098037 A1 | 5/2003 | Dougan et al. | |
| 2003/0140936 A1 | 7/2003 | Yuhara | |
| 2004/0200497 A1 | 10/2004 | Thorpe et al. | |
| 2005/0205107 A1 | 9/2005 | Ochs | |
| 2009/0120454 A1 | 5/2009 | Ochs et al. | |

FOREIGN PATENT DOCUMENTS

| | | |
|---|---|---|
| EP | 610227 B | 8/1994 |
| EP | 904744 A | 3/1999 |
| EP | 1579822 A | 9/2005 |
| EP | 1769773 A | 4/2007 |
| EP | 2153798 A | 2/2010 |
| JP | 8173243 A | 7/1996 |
| WO | WO 93/04641 A | 3/1993 |
| WO | WO 00/44302 A | 8/2000 |
| WO | WO 01/12100 A | 2/2001 |
| WO | WO 02/32341 A | 4/2002 |
| WO | WO 03/043523 A | 5/2003 |

* cited by examiner

APPARATUS FOR MANUFACTURE OF SINGLE-USE DENTAL FLOSS HOLDERS

FIELD OF THE INVENTION

This invention relates to an apparatus used to manufacture single-use floss holders that contain wax coated dental floss.

BACKGROUND OF THE INVENTION

A number of single-use flossing devices are know and commercially available. Such devices typically have a floss holder that includes two spaced-apart arms extending upwardly, or outwardly, from a base to form a generally U-shaped configuration with the floss attached at each end to one of the arms and spanning the distance between the spaced-apart arms. The devices also include a handle portion in association with the floss holder.

In some devices, the dental floss holder itself is removable from the handle portion and thus replaceable. Such devices generally include a handle with a head portion designed to receive and hold the dental floss holder. In use, the dental floss holder is attached to the head portion of the handle and the floss is inserted between teeth. After flossing, the dental floss holder is removed from the head of the handle and replaced with a new dental floss holder. Such devices are shown in, for example, U.S. Pat. Nos. 5,483,982, 7,059,334, 7,174,904 and 7,325,554, the content each of which is hereby incorporated by reference in its entirety. It is noted that devices exemplified in such patents and commercial products made according to the disclosures of such patents do not use wax coated yarns. In other devices, the dental floss holder is integral with the handle portion to form a unitary device, such that the entire device may be disposed of after completion of flossing.

In one method of manufacturing such devices and attaching the floss to the arms of the floss holders, the floss holder, whether removable from or integral with the handle, typically is molded from plastic around the uncoated floss to provide the generally U-shaped floss holder having the floss attached to and extending between the spaced-apart arms of the holder. As noted, holders may be molded integral with a handle portion to form a unitary device, or may be molded with means to rigidly connect the detachable floss holder to the head of a handle which is configured to receive the detachable floss holder.

Flosses in general must be capable of passing between several teeth without significant fraying or breaking during insertion of the floss between the teeth and also during the up and down motion of the flossing process. For this reason, some yarns are made from an extremely strong material, such as ultra high molecular weight polyethylene (UHMWPE). Furthermore, multifilament yarns that are highly twisted, i.e. having more than two turns per inch, to hold adjacent fibers, or filaments, tightly together during the flossing process also are used. Twists of 3 or 4 twists per inch are typical. Makers of traditional floss sold in conventional dispensers have found consumers prefer softer flosses that slide more easily between teeth and are gentler on gums. For this reason, manufactures have reduced or eliminated twist in such multifilament yarns. However, this typically results in an increase in fraying and breaking. In order to maintain reduced fraying and breaking, manufactures have impregnated the space between fibers with soft polymers such as microcrystalline wax or beeswax.

While coated multifilament yarns are suitable for use when dispensed from a conventional floss dispenser, where the floss is wrapped around a spool, wax coated multifilament flosses are not known to be used in commercial single-use floss devices as described above. This is due, in part, to difficulties associated with the manufacture of such devices using wax coated multifilament yarns.

In summary, there is a need for a single-use flossing device that uses flosses that slide more easily between teeth and are gentler on gums, while maintaining strength to reduce fraying and breakage, as well as methods and apparatus for making such single-use devices. As described below, it now has been discovered how to provide single-use flossing devices using wax coated dental floss.

SUMMARY OF THE INVENTION

The invention concerns a mold for forming a single-use floss holder containing a length of dental floss having a wax composition applied thereto, the mold including a first part having a first cavity disposed therein, the first cavity defined by a bottom base surface and a peripheral sidewall, and including a base portion, first and second spaced-apart portions having proximal and distal sections and extending from the base portion, and a second part having a second cavity disposed therein, the second cavity defined by a bottom base surface and a peripheral sidewall, and including a base portion, first and second spaced-apart portions having proximal and distal sections and extending from the base portion and terminating in the distal section; and a groove having an aspect ratio of about 10:1 or greater and having first and second terminal sections and a mid-section, the groove extending an entire width of the second part, where the first and second terminal sections of the groove traverse and are coincident with the distal section of the first and second spaced-apart portions of the second cavity, respectively.

DETAILED DESCRIPTION OF THE INVENTION

Figure 1:
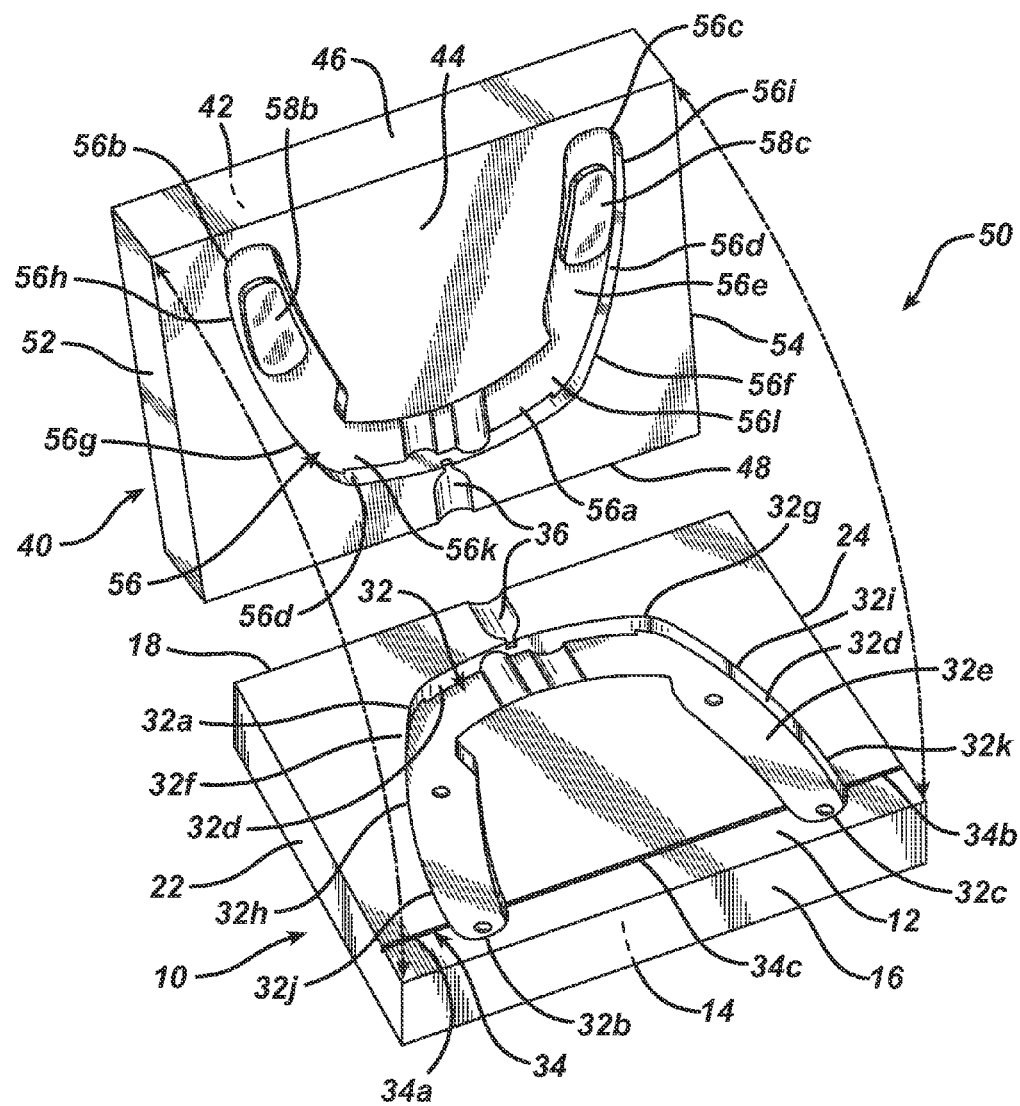
FIG. 1 is a perspective view of a conventional mold used to prepare conventional single-use floss holders.

In attempting to use conventional molds that are used for making conventional single-use floss holders that use floss that does not include a wax coating, problems were discovered that prevented the use of such molds to make floss holders that utilize wax coated floss. It was found that wax from the coated dental floss builds up in the groove of the conventional mold where the length of floss is held between the two mold halves at the time of molding the floss holder about the floss. The degree of buildup in the groove is dependent upon not only the amount of wax on the floss, but also on the amount of wax actually in contact with the mold surface.

It was discovered that, as the groove filled with residual wax from the dental floss, there was less and less room for the floss to nest within the groove in the mold so that the floss holder may be molded around the floss. Eventually, wax was deposited in the groove of the conventional mold to an excessive level, which contributed to floss breakage, thus causing the molding operation to stop. With the level of wax used on conventional waxed flosses, it was found that buildup and breakage using conventional molds typically occurred after about 5 to 10 molding cycles, thus making commercial manufacture of such floss holders with conventional molds cost prohibitive.

In addition to the contribution to floss breakage caused by wax buildup, other factors limiting commercial feasibility of single-use flossing devices using wax coated yarns exist. One issue is the melting problem encountered during the insert molding operation. Typically, conventional single-use flossing heads, or floss holders, are made from polypropylene that has a melt temperature around 160° C. The floss around which the floss holders are molded is made from ultra high molecular weight polyethylene (UHMWPE) having a melt temperature around 125° C. Extrusion barrel temperatures of 180° C. to 190° C. are typical and insertion nozzle temperatures of up to 325° C. are used to inject the resin for forming the floss holder into the mold. This means that hot molten resin is pumped into a mold and contacts the floss that has a much lower melt temperature. As such, heat may be transferred to the floss at levels sufficient to melt the floss.

In the case of highly twisted UHMWPE floss that does not contain a wax coating, the molten resin used to form the floss holder does not penetrate the floss due to the twist and tightness of the floss and thus there is an insufficient amount of heat transferred to melt the floss. However, in the case of wax coated UHMWPE floss, it is believed that the wax acts as a heat transfer agent between the molten resin and the UHMWPE and partial or complete melting of the floss may occur where the resin contacts the floss.

The present invention provides a solution to these significant problems associated with conventional molds and methods used when attempting to make single-use floss holders that utilize dental floss that has a wax coating composition applied thereto. Molds according to the present invention useful for forming single-use floss holders containing a length of dental floss that has a wax composition applied thereto solve problems associated with heat transfer attributable to the wax composition and/or excessive wax buildup in the floss groove of the mold. As used herein, dental floss, or floss, include various forms of dental floss, including multifilament yarns, whether twisted or untwisted, monofilament dental tape, e.g. core sheath dental tapes, and monofilament elastomeric dental tape formed by extrusion of the elastomeric material.

Molds according to the present invention may be made from hardened tool steel, although aluminum may also be used. The molds include a first part and a second part, which also may be considered as top and bottom parts, which are brought together during formation of the dental floss holder of the present invention. The first part comprises a first cavity defined by a bottom base surface and a peripheral wall. The first cavity includes a base portion and first and second spaced-apart portions having proximal and distal sections extending from the base portion. Each spaced-apart portion terminates in the distal section thereof. The first cavity may be generally V-shaped or U-shaped, for example. The base portion may be substantially horizontal and comprise a mid-section and first and second terminal sections, as shown herein below. In certain embodiments, the first and second spaded-apart portions are substantially lateral and disposed substantially transverse to the substantially horizontal base portion. In this embodiment, the lateral spaced-apart portions extend from the first and second terminal sections, respectively, of the base portion to form the generally U-shaped cavity.

The second part comprises a second cavity disposed therein, substantially corresponding in both shape and size to the first cavity in the first part. The second cavity in the second part is defined by a bottom base surface and a peripheral sidewall. The second cavity includes a base portion and first and second spaced-apart portions having proximal and distal sections extending from the base portion. Each spaced-apart portion terminates in the distal section thereof. In certain embodiments, the first and second spaded-apart portions are substantially lateral and disposed substantially transverse to the substantially horizontal base portion. In this embodiment, the lateral spaced-apart portions extend from the first and second terminal sections, respectively of the base portion to form the generally U-shaped cavity.

Molds used to form floss holders of the present invention utilize grooves specifically designed to prevent buildup of the wax coating within the groove, thus minimizing or alleviating the problems associated with wax buildup. The groove comprises first and second terminal sections and a mid-section. The groove may be located in either the first or the second part, although as shown and discussed herein it is disposed in the second, or bottom, part. The groove extends the entire width of the second mold part, with the first and second terminal sections of the groove traversing, or spanning, and being coincident with the distal section of the first and second spaced-apart portions, respectively.

Floss grooves in molds according to the present invention have an aspect ratio (width:depth) of about 10:1 or greater, or between about 10:1 to about 100:1, or between about 25:1 to about 75:1, or about 50:1. The mid-section of the groove may be wider and/or deeper than the respective terminal sections to reduce contact with the length of wax coated dental floss during molding of the floss holders of the present invention. For example, the mid-section may be from about from about 2 to about 10 times deeper and/or from about 1.2 to about 1.5 times wider than the terminal sections. A groove for a typical 400 denier yarn would be about 0.010 inch radius groove cut of about 0.02 inch deep and about 0.020 inch wide. Conventional molds for forming conventional single-use flossing devices using uncoated floss utilize grooves typically having an aspect ratio (width:depth) between about 1:1 and about 4:1. The cross-sectional configuration of the groove may vary from a semi-circle to almost V-shaped to easily capture and compact a length of floss between the mold halves. The conventional groove also may have a mid-section and terminal sections, where the mid-section may be wider than the terminal sections. The cross-sectional area of the groove is essentially the same cross-sectional area of the floss.

While the aspect ratios and cross-sectional configuration of grooves of conventional molds and grooves of molds according to the present invention are vastly different, the overall volume of the grooves is approximately equal. The cross-sectional configuration of grooves used in molds according to the present invention is substantially rectangular and has a substantially flat bottom surface, as compared to cross-sectional configurations of grooves in conventional molds. This prevents or minimizes buildup of wax in the groove, while at the same time providing for greater tolerance in placement of the length of floss within the groove of the mold, thus allowing for some lateral misalignment of the floss in the groove.

As such, problems associated with conventional molds relating both to breakage and misalignment of floss are synergistically improved.

In embodiments where the wax composition may serve as a heat transfer agent, the mold may further include one or multiple heat sinks disposed proximate each of the first and second terminal sections of the groove that is coincident with the distal section of the first and second lateral spaced-apart portions, respectively. As used herein, "heat sink" means an object that absorbs and dissipates heat from another object, e.g. the length of coated dental floss, using thermal contact, which contact may be either direct or radiant. As used herein, "proximate each of the first and second terminal sections" means that the heat sink is disposed either in contact with the terminal section of the groove, or at a distance sufficiently close to the terminal section of the groove, such that it is effective to transfer heat away from the length of dental floss to the heat sink, thereby reducing breakage in the floss due to melting during molding of the floss holder about the floss. During molding of the floss holder, the heat sink is proximate the terminal ends of the length of dental floss disposed in the distal portions of the spaced-apart portions of the cavity. As with the groove, the heat sink is in contact with, the length of dental floss, or at a distance sufficiently close to the length of dental floss, such that it is effective to transfer heat away from the length of dental floss. The heat sink may shield one side or both sides of the floss from the molten resin forming the floss holder, as well as direct the flow of resin around the floss.

Figure 2:
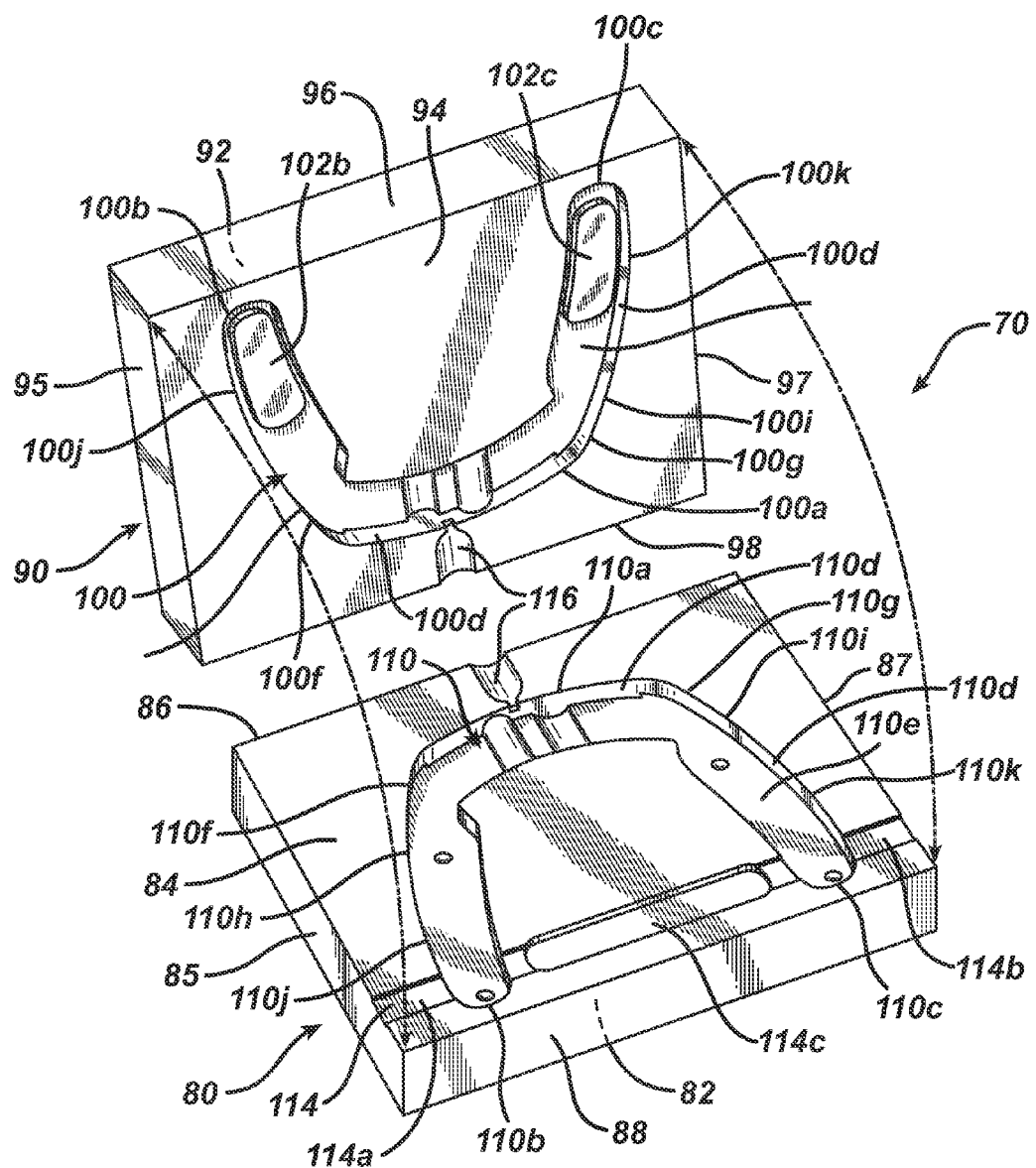
FIG. 2 is a perspective view of a mold according to the present invention.

One embodiment of a heat sink according to the invention is shown in FIG. 2. As shown therein, a projection is disposed in the first cavity of the first part. The projection serves, on the one hand, to form a cavity in the final floss holder for holding, e.g. a flavor composition. In addition, the projection is located in the first cavity of the first part such that it is proximate the terminal sections of the groove in the second part when the two parts of the molds are brought together. As a result, the heat sink is proximate the length of coated dental floss during molding of the dental floss holder and serves as a heat sink. While the conventional mold shown in FIG. 1 also includes the projection disposed in the first cavity to form a cavity in the floss holder for holding, e.g. a flavor composition, when the mold parts are brought together, the projection is not proximate the groove. As a result, the length of floss held in the conventional mold is not proximate the projection during molding and the projection does not serve as a heat sink. In embodiments of the invention requiring a heat sink, the relative location of the projection and groove in the mold then are critical in assuring that the projection will serve as a heat sink during formation of the floss holder. While FIG. 2 shows the projection in a position that will serve as a heat sink, in those embodiments of the invention that do not require a heat sink, the projection need not be proximate the terminal sections of the groove.

Alternatively, a pressure release pin could function as a heat sink in the mold. In this case, the pin is proximate the terminal sections of the groove and contacts, or shields, one side of the wax coated floss until the final pressure is reached inside the mold, at which point the pressure forces the pin to recede into the body of the mold, thereby closing the cavity area. As with the molds themselves, the heat sink may be made from hardened tool steel, although aluminum may also be used.

Floss holders produced utilizing molds according to the present invention may be made integral with a handle, such as unitary single-use disposable flossing devices, which may then be disposed of after use. Alternatively, floss holders produced according to the present invention may be made with a fitment to allow the floss holder to be rigidly, but removably, attached to a separate handle. The floss holder itself then would be disposable and the handle re-usable.

In one embodiment, the floss holder is generally U-shaped and includes a substantially horizontal base portion having a mid-section and first and second terminal sections. First and second substantially lateral spaced-apart arms are integral with and substantially transverse to the base portion. The lateral arms each have a proximal end integral with the first and second terminal sections of the base portion, respectively. Each lateral arm terminates in a distal section thereof. The arms extend from the first and second terminal sections of the base portion, respectively, thus forming the generally U-shaped configuration. A length of floss having a wax composition applied thereto extends between the spaced-apart arms and is rigidly attached at each end of the floss in the distal section of each of the spaced-apart arms. The floss may be anchored in the spaced-apart arms by the use of knots formed on the outside of the respective arms, formed by heating the floss above the melting point, thus forming beads of melted floss on the outside surfaces of the respective spaced-apart arms. The holder can be made from a polymer such as polypropylene, polystyrene, polyethylene or other similar molding materials.

The length of floss that extends between the lateral spaced-apart arms may be a made from a multifilament yarn, or a monofilament floss, or tape. Because of the need to pass between multiple teeth, the floss needs to be very fray resistant. For this reason, the preferred material of the multifilament yarn is Ultra High Molecular Weight Polyethylene (UHMWPE) with a denier of about 400 and a filament size of approximately 1 dpf. Filaments larger than 1 dpf will also work, but more coarse filaments result in increased insertion force between teeth and are less desirable. Filaments below 1 dpf filament would also be useable although, no manufacturer currently makes such a filament. Yarns of this nature are supplied under the trade name DYNEEMA by companies such as DSM (DSM Dyneema B.V., Urmond, the Netherlands), and designated as SK65. Other materials could be used, but the high strength and fine filament of the UHMWPE make it the most desirable of materials.

The uncoated multifilament yarns used on known single-use flossing devices are highly twisted, e.g. more than two turns per inch, to hold adjacent fibers tightly together during the flossing process, thus preventing fraying. Twists of 3 or 4 twists per inch are typical. In the present invention, high twisted or low twist yarn may be used. Low twisted yard in herein defined as being twisted less than 2 twists per inch of yarn, and ideally should be twisted about 1.5 twists per inch. This provides a good balance between soft feel, fray resistance and insertion force. No twist yarn with air entangled nodes also may be used in the current invention.

In addition to multifilament yarns, flosses manufactured using molds according to the present invention may be made from monofilament tape, such as are disclosed in US2009/0120454 A1, the contents of which is hereby incorporated by reference in its entirety. Such monofilament dental tapes include a core body having an aspect ratio of greater than about 5:1 and a first cleaning surface and a second cleaning surface opposite the first cleaning surface, where at least one of the first and second cleaning surfaces includes a plurality of ribs disposed along the length thereof, and where the ratio of the width of the dental tape to the thickness of the dental tape is from about 3:1 to about 25:1.

Elastomeric materials that may be used to form such dental tape include, but are not limited to, polyamide-polyether block copolymers sold under the tradename PEBAX (Ato Chimie, Hauts-de-Seine France), such as PEBAX 7033, 5533 MX1205, 4033, 3533, and 2533; polyester-polyether block copolymers and polyester-polyester block copolymers sold under the tradename HYTREL (E. I. du Pont de Nemours & Co., Wilmington, Del.), such as HYTREL 7246, 5556, and 4056; aliphatic thermoplastic polyurethane elastomers sold under the tradename TECOFLEX (Lubrizol Advanced Materials, Inc., Cleveland Ohio); aromatic thermoplastic polyurethane elastomers sold under the tradename PELLETHANE (Dow Chemical Co., Midland, Mich.); and thermoplastic polyolefin elastomer sold under the name MULTI-FLEX (Dow Chemical Co., Midland, Mich.). Non-elastomeric materials from which the dental tape can be made include nylon or polytetrafluoroethylene (PTFE).

The length of dental floss used in the single-use floss holders of the present invention has a wax composition applied thereto to slide more easily between teeth and to be gentler on the gums. In addition to better sliding between teeth, the wax composition also serves to bind the filaments of a low twist yarn together, thus preventing fraying. The dental floss may contain about 10 percent or more, for example about 25 percent or more, of the wax composition applied thereto, based on weight of the length of dental floss. In certain embodiments, the length of dental floss may contain from about 25 percent to about 50 percent of the wax composition applied thereto, based on the weight of the length of dental floss.

The coating on the floss comprises waxes and may include further additives. Additives to the wax composition are used to prevent transfer of coatings to the molds and for better adhesion of the wax composition to the plastic comprising the molded head, i.e. floss holder. An exemplary wax useful in the wax compositions for the floss is Multiwax W-445, made by the Petroleum Specialties Group of Witco Corp. (New York, N.Y.), although other grades of microcrystalline wax (MCW) having melting points from about 76° C. to about 85° C. and a hardness of about 14 to about 25 dm would suffice. In addition or alternatively, beeswax, such as Strahl and Pitsch white beeswax NF-SP422 and similar waxes, may be used. In some embodiments, the wax composition comprises from about 10 percent to about 95 percent by weight of microcrystalline wax, based on total weight of the wax composition. Additives to the wax composition include items that make the wax less sticky and/or increase the floss adhesion within the head, while not appreciably decreasing the pliability of the bundle of fibers. This allows the floss to move freely with minimal separation of individual fibers from the bundle during the rigors of flossing. One such additive is an ethylene vinyl acetate copolymer, such as A-C 400 grade manufactured by Honeywell (Honeywell International, Morristown, N.J.). Other additives also may be used, such as polyethylene homopolymers from Honeywell, e.g. A-C 617. Polymers useful as additives will exhibit a combination of compatibility with the wax, the appropriate melt temperature, a low viscosity and the appropriate hardness. The polymers having a melt temperature between about 80° C. and 120° C., a viscosity below about 600 cps and a hardness (ASTM D-5) between about 1 and about 9, appear to be advantageous.

While the flossing device can be made successfully without any additive, it may be desirable to use an additive to increase the adhesion of the floss within the floss holder. For example, the wax composition may include from about 5 percent to about 40 percent by weight of the additive, or about 20 percent by weight, based on total weight of the composition. While other ranges may work, about 20 percent provides a good balance between pliability, softness, slideability, adhesion within the floss holder and minimum wax buildup within the molding operation.

In processes for making a single-use dental floss holder according to the present invention, which comprise a length of dental floss having a wax composition applied thereto, a length of dental floss having a wax composition applied thereto is provided. Uncoated yarn or dental tape, either multifilament or monofilament, is supplied in rolls typically weighing approximately 1 to 5 kilograms. Multifilament yarn may have a twist, no twist, or be air entangled, each utilizing known commercial technologies.

The supply rolls holding the uncoated dental floss are passed through standard floss coating equipment, where wax coatings are applied, and the coated floss is rewound onto supply rolls for further processing. One skilled in the art will recognize that any wax coating process and coating equipment conventionally used to prepare conventional wax coated dental floss may be employed. The temperature of the wax coating composition and the application die used in the coating process is dependent upon the coating being applied. Typically for microcrystalline wax coatings, it is desirable to apply the coating at temperatures significantly higher than the melting point of the wax in order to achieve good penetration of the wax into the inner fibers of the yarn, in the case of the multifilament yarn. This is typically 90° C. to 95° C. for Witco W-445. For a mixture of about 80 percent microcrystalline wax and about 20 percent EVA, this temperature is typically about 95° C. to about 115° C. Distributing the wax into the inside of the multifilament yarn bundle provides enhanced binding of internal fibers and also minimizes wax on the surface of the floss, which can contribute to wax buildup in the groove of the mold used to form the floss holder, thus contributing to floss breakage during insert molding.

The supply roll holding the wax coated floss is then provided to an insert molding machine that includes a mold having a cavity for receiving molten plastic material and a groove for receiving a length of the wax coated dental floss in one half of the mold. The groove in the mold has an aspect ratio of about 10:1 or greater. The floss is pulled through the two open mold halves and positioned in the groove of the mold such that the terminal ends of the length of dental floss span the respective distal sections of the cavity in the mold half containing the groove. The mold optionally may include a heat sink or heat sinks proximate the groove and length of wax coated dental floss. The mold halves are then brought together and the molten plastic is then injected via an injection nozzle into the cavity of the mold, thus forming flossing heads, or floss holders, around the terminal ends of the floss.

The temperature of the resin entering the mold affects the retention force of the floss within the head. An optimum temperature of the resin is one in which no melting of the floss occurs. A temperature higher than optimum results in lower retention force, as part of the floss within the head is melted during the molding process, thus reducing the retention force. The temperature of the resin entering the mold is affected by the four controllable temperature points within the extrusion barrel, the nozzle temperature and the hot manifold temperature. These temperatures are selected such that the force required to pull the floss from the ends of the finished floss holder is about four pounds or greater, e.g. about 5 pounds or greater. If the temperature of the resin is too high, the force required to pull the wax coated dental floss from the respective lateral portions of the floss holders will not be sufficiently high. The actual temperature selected will depend on factors such as the particular dental floss, the concentration of wax coating applied to the dental floss, the composition of the wax coating and the presence, or not, of a heat sink located proximate the groove of the mold and the length of dental floss positioned within the mold. In certain embodiments, the temperature of the injection nozzle will be about 300° C. or less, or about 275° C. or less, or from about 210° C. to about 290° C., or from about 220° C. to about 270° C. It has been discovered that by using a heat sink, as described herein, in combination with a groove having an aspect ratio of about 10:1 or greater, the variation in the pull out force can be reduced, while also improving the minimum pull out force expected to pull the floss from the floss holder.

The molded floss holders are typically attached to a cold runner for cooling and to at least to strands of floss which are used to extricate the molded parts from the mold once the parts have solidified upon cooling and after the mold is opened. Each attached group of floss holders is then separated from the next group by cutting the floss between the respective groups. An open flame is used to cut the floss between adjacent holders. This burning process melts and shrinks the excess floss back to the exterior of the lateral arm of the floss holder, thus forming a knot in the terminal section of the floss at exterior side of the distal section of the lateral arm, which holds the floss in place.

As mentioned earlier, an issue with making single-use flossing heads, e.g. floss holders, having wax coated floss is the problem of molding molten materials, e.g. plastics, around the wax coated floss. One the one hand, wax from the floss builds up in the groove of the mold where floss is held between the mold halves. One the other hand, the wax may serve as a heat transfer agent, contributing to melting of the floss during the molding operation. The molds of the present invention overcome this problem.

FIG. 1 is a perspective view of a prior art mold used to manufacture conventional single-use floss holders utilizing dental flosses that do not contain a wax coating. Mold 50 has first part 40 and second part 10. First part 40 is a rectangular prism, with top face 42, bottom face 44, and side faces 46, 48, 52, and 54. First part 40 further includes generally U-shaped first cavity 56 disposed therein. Cavity 56 is defined by peripheral sidewall 56d and cavity bottom surface 56e, with sidewall 56d extending between the plane of cavity bottom surface 56e and the plane of bottom face 44. Cavity 56 includes horizontal base cavity portion 56a, having first 56k and second 56l terminal sections, and substantially lateral spaced-apart cavity portions 56b and 56c, each having proximal sections 56f, 56g and distal sections 56h, 56i, substantially transverse to and extending in the same direction away from the first 56k and second 56l terminal sections of base cavity portion 56a, to form the generally U-shaped configuration. Projections 58b and 58c are disposed within lateral cavity portions 56b and 56c, respectively, for forming a cavity in the floss holder for containing, for example, compositions containing flavors.

Second part 10 has top face 12, bottom face 14, and side faces 16, 18, 22, and 24. Second part 10 is a rectangular prism, and has generally U-shaped second cavity 32 disposed therein. Cavity 32 is defined by peripheral sidewall 32d and cavity bottom surface 32e, with sidewall 32d extending between the plane of cavity bottom surface 32e and the plane of top face 12. Cavity 32 includes base cavity portion 32a, having first 32f and second 32g terminal sections, and substantially lateral spaced-apart cavity portions 32b and 32c, each having proximal sections 32h, 32i and distal sections 32j, 32k, substantially transverse to and extending in the same direction away from first 32f and second 32g terminal sections of base cavity portion 32a, to form the generally U-shaped configuration.

Floss groove 34 is situated transverse of lateral cavity portions 32b and 32c, with the location of groove 34 corresponding to the desired location of where the length of floss spans cavity portions 32b and 32c. Groove 34 has mid-section 34c and terminal sections 34b and 34a. Injection port 36 is located within rear side faces 18 and 48 of first part 40 and second part 10, respectively. During the injection molding process, molten resin passes through injection port 36 and fills the mold cavity formed by first cavity 56 and second cavity 32 when first 40 and second 10 mold parts are brought together, thus embedding the length of floss in the floss holder.

Figure 1A:
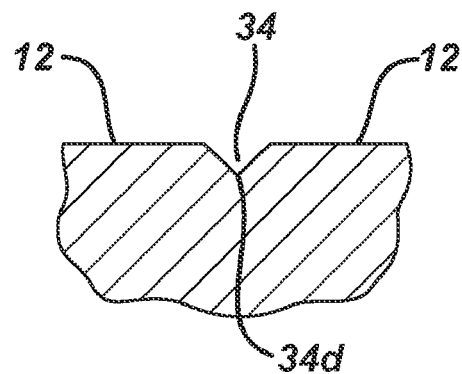
FIG. 1a is a cross-sectional view of the groove depicted in FIG. 1.

FIG. 1a is a cross-sectional side view of a terminal section of groove 34. As shown, groove 34 has a substantially V-shaped or semi-circular cross-sectional configuration. The bottom 34d of groove 34 forms a trough-like configuration in which the length of dental floss is positioned during manufacture of the conventional dental floss holder.

Figure 1B:
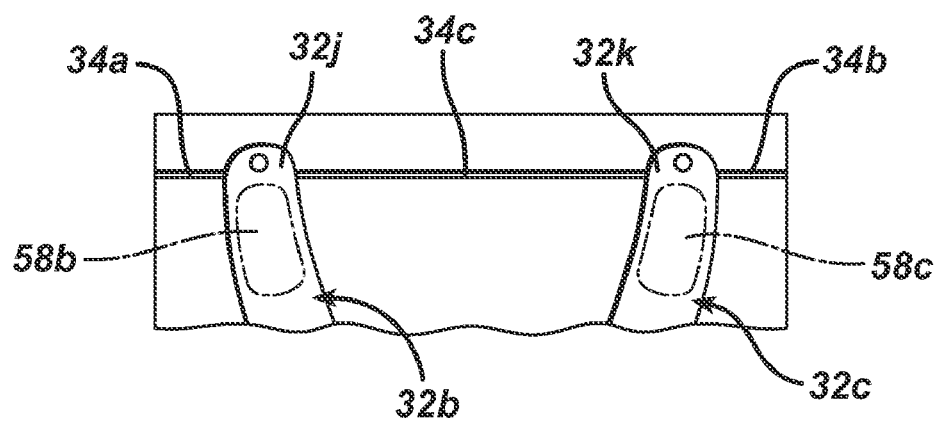
FIG. 1b is a top plan view of the distal sections of the lateral cavities in the second mold part as depicted in FIG. 1, with projections of the first part shown in phantom as they would be positioned when first and second mold parts are brought together.

FIG. 1b is a top plan view of distal sections 32j and 32k of lateral cavities 32b and 32c, respectively, as depicted in FIG. 1. Terminal sections 34a and 34b of groove 34 traverse, or span, distal sections 32j and 32k of lateral cavities 32b and 32c, respectively. Projections 58b and 58c of the first part are shown as they would be positioned within lateral cavities 32b and 32c, respectively, when the two halves of the mold are brought together. As shown, projections 58b and 58c are not proximate terminal sections 34a or 34b of groove 34. Consequently, projections 58b and 58c do not function as a heat sink in the prior art mold.

FIG. 2 is a perspective view of a mold according to the present invention. Mold 70 has first part 90 and second part 80. Mold 70 may be made from hardened tool steel, although aluminum may also be used. First part 90 is a rectangular prism, with top face 92, bottom face 94, and side faces 95, 96, 97, and 98. First part 90 further includes generally U-shaped first cavity 100 disposed therein. Cavity 100 is defined by peripheral sidewall 100d and cavity bottom surface 100e, with sidewall 100d extending between the plane of cavity bottom surface 100e and the plane of bottom face 94. Cavity 100 includes base cavity portion 100a, having first 100f and second 100g terminal sections, and substantially lateral spaced-apart cavity portions 100b and 100c, each having proximal sections 100h, 100i and distal sections 100j, 100k, substantially transverse to and extending in the same direction away from the first and second terminal sections of base cavity portion 100a, to form the generally U-shaped configuration. Projections 102b and 102c are disposed within lateral cavity portions 100b and 100c, respectively, for forming a cavity in the floss holder for containing, for example, compositions containing flavors.

Second part 80 has top face 82, bottom face 84, and side faces 85, 86, 87 and 88. Second part 80 is a rectangular prism and has generally U-shaped cavity 110 disposed therein. Cavity 110 is defined by peripheral sidewall 110d and cavity bottom surface 110e, with sidewall 100d extending between the plane of cavity bottom surface 110e and the plane of bottom face 84. Cavity 110 includes base cavity portion 110a, having first 110f and second 110g terminal sections, and substantially lateral spaced-apart cavity portions 110b and 110c, each having proximal sections 110h, 110i and distal sections 110j, 110k, substantially transverse to and extending in the same direction away from the first 110f and second 110g terminal sections of base cavity portion 110a, to form the generally U-shaped configuration.

Floss groove 114 is situated transverse of lateral cavity portions 110b and 110c, with the location of groove 114 corresponding to the desired location of where the length of floss spans cavity portions 110b and 110c. The location of groove 114 is such that it is proximate projections 102b and 102c during molding of the floss holder. In this embodiment, given the proximate location of projections and floss groove, the projections serve as a heat sink to dissipate heat away from the length of floss during molding. In floss holders made utilizing such molds, the length of coated floss is proximate the cavity of the floss holder formed by projections 102b and 102c. Injection port 116 is located within rear side faces 98 and 86 of first part 90 and second part 80, respectively. During the injection molding process, molten resin passes through injection port 116 and fills the mold cavity formed by first cavity 100 and second cavity 110 when mold parts 90 and 80 are brought together, thus embedding the length of floss in the floss holder such that at least a portion of the length of floss is proximate the cavity formed in the floss holder. Although shown as a single-part mold, multiple-part molds having the capacity to form on the order of 20 or more individual floss holders may be used in the manufacture of such floss holders.

Figure 2A:
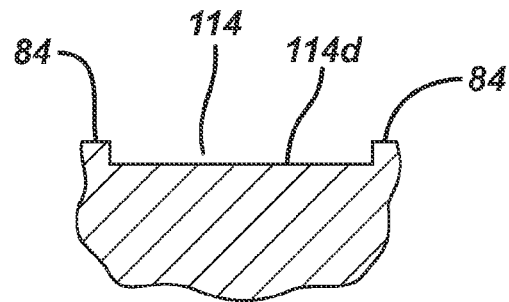
FIG. 2a is a cross-sectional view of the groove depicted in FIG. 2.

FIG. 2a is cross-sectional side view of groove 114. As shown, groove 114 has a substantially rectangular cross-sectional configuration having a substantially flat bottom surface 114d in which the length of dental floss is positioned during manufacture of the dental floss holder of the present invention.

Figure 2B:
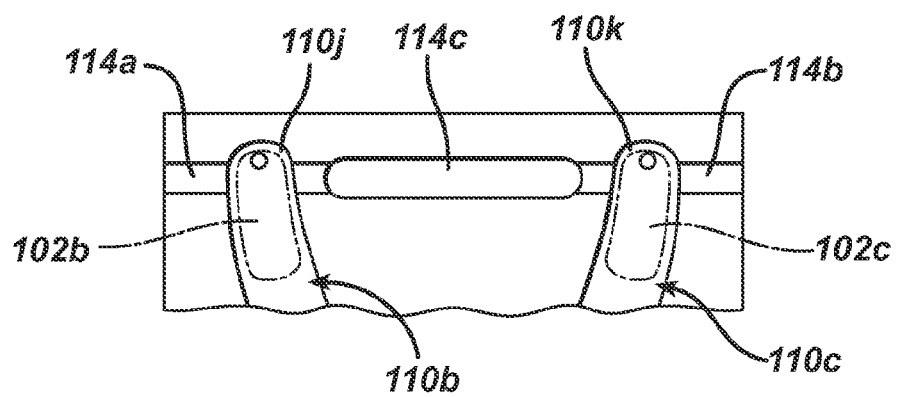
FIG. 2b is a top plan view of the distal sections of the lateral cavities in the second mold part as depicted in FIG. 2, with projections of the first part shown in phantom as they would be positioned when first and second mold parts are brought together.

FIG. 2b is a top plan view of distal sections 110j and 110k of lateral cavities 110b and 110c, respectively, as depicted in FIG. 2. Terminal sections 114a and 114b of groove 114 traverse, or span, distal sections 110j and 110k of lateral cavities 110b and 110c, respectively. Projections 102b and 102c of the first part are shown as they would be positioned within lateral cavities 110b and 110c, respectively, when the two halves of the mold are brought together. As shown, projections 102b and 102c are proximate terminal sections 114a or 114b of groove 114. Consequently, projections 102b and 102c function as a heat sink in the mold during manufacture of dental floss holders according to the present invention.

The pull out force is defined as the amount of force it would take to pull the floss from a flossing head, i.e. a floss holder, or the amount of force a user would have to apply to a flossing head to loosen the floss such that the holder is inoperable. The minimum pull out force of the floss preferably is above four pounds and more preferably above five pounds. The technique to measure the force of removal is typically accomplished by attaching the floss holder to an Instron or similar device. A hook attached to the moveable side of the Instron is placed in the middle of the floss holder. The hook is then slowly moved up, thus hooking the mid-section of the floss in the process. The hook moves up at a constant speed of approximately 10 inches per minute applying an increasing force until it ultimately results in one side of the floss pulling through the U-shaped head. This simulates the force the user would have to exert on the floss in order for the flossing device to become inoperative.

Examples are provided below to further illustrate the advantages of the present invention. The invention should not be construed as being limited to the specific detail set forth herein.

EXAMPLE 1

A mold having a first, i.e. top, part and a second, i.e. bottom, part was created, each part containing eight cavities for producing single-use floss holders, 4 cavities on each side, with a cold runner connecting the cavities. In one section of the top part of the mold, the first part was similar to that shown in FIG. 2, where a projection was located such that it served as a heat sink and formed a cavity in the final floss holder. In the other section of the first part, no projection was used and thus there was no cavity in the final floss holder. The second part of the mold included grooves machined into the facing thereof for receiving the length of floss when the mold halves were closed. Two different configuration floss grooves similar to those shown in FIGS. 1 and 2 were used for comparison. A conventional groove (designated Groove A below) having a cross-sectional semi-circle configuration with approximately a 0.010-inch radius was machined into the mold half such that the width at the facing of the mold was 0.020-inch and the depth from the facing to the bottom of the groove was 0.010-inch, thus providing an aspect ratio (w/d) of 2:1. The other groove used according to the present invention (designated Groove B below) had a substantially rectangular cross-sectional configuration and was 0.100 inch wide and 0.002-inch deep, thus providing an aspect ratio (w/d) of 50:1.

A number of flosses, both with and without wax coating applied thereto, were tried on both sides of the mold to compare performance of Groove A to Groove B. The molding conditions were as follows:
Insert Pressure 500 lbs
Hold Pressure 100 lbs
Barrel and manifold temperatures 182° C.
Insert Nozzle Temperature 315° C.
Cycle time 11.4 seconds In the first set of trials, prototype single-use floss holders were formed using a 400 denier UHMWPE multifilament floss having a variety of coatings applied thereto. The results of the molding trials are summarized in Table 1.

TABLE 1

| Trial | Floss | Results of Molding Trials |
|---|---|---|
| 1 | 400 denier UHMWPE, 3 twists, no wax coating | Ran well with Groove A Ran well with Groove B |
| 2 | 400 denier UHMWPE with 1.5 twists with 25% wax coating (MCW (60%), PE 617 (40%)) | Created wax buildup in Groove A requiring cleaning after approximately 50 cycles No perceivable buildup in Groove B. |
| 3 | Same as 2 except coating was 80% MCW and 20% PE | Created wax buildup in Groove A No perceivable buildup in Groove B |
| 4 | Same as 2 except coating was 60% MCW and 40% EVA | Created wax buildup in Groove A No perceivable buildup in Groove B |
| 5 | Same as 2 except coating is 80% MCW and 20% EVA | Created wax buildup in Groove A No perceivable buildup in Groove B |
| 6 | Same as 2 except coating is 90% MCW and 10% EVA | Created wax buildup in Groove A No perceivable buildup in Groove B |

NOTES:
MCW is microcrystalline wax, PE is polyethylene homopolymer, and EVA is Ethylene Vinyl Acetate Copolymer.

Table 1 shows that UHMWPE floss containing no wax coating resulted in no processing issues for either groove configuration. When single-use floss holders were formed with wax-coated UHMWPE, however, wax coating buildup occurred in the comparative Groove A, whereas little to no coating buildup occurred in the inventive Groove B.

Next, a short manufacturing run was performed using only the prototype mold side including Groove B to make single-use flossing devices using a 400-denier SK-65 UHMWPE multifilament floss with 1.5 twists and having a 49 percent coating weight of a wax coating composition comprising 60 percent MCW and 40 percent PE-617. This run was to test the durability of the process. After 1.5 hours of run time, the mold was opened and examined for buildup and debris. While a small amount of buildup was seen, it was not sufficient to result in process stoppage or to negatively impact the molding process.

EXAMPLE 2

Molds used in Example 1 with Groove B (50:1 aspect ratio) were used to prepare single-use dental floss holders utilizing two different flosses. The first was a highly twisted multifilament floss yarn. This floss was an unwaxed UHMWPE DSM SK 65 yarn with 3 twists per inch. The second floss was UHMWPE DSM SK-65 yarn, 400 denier with 1.5 twists per inch, and included 25 percent by weight of a coating containing 80 percent microcrystalline wax and 20 percent Honeywell EVA PE400. The production conditions were as follows:

Insertion Pressure: 375 lbs
Hold Pressure: 100 lbs
Barrel and manifold temperatures 182° C.
Insert Nozzle Temperature 315° C.
Cycle Time: 11.4 seconds The Average and Minimum Expected force required to pull the floss out of the floss holder is shown on Table 2. The Minimum Expected value for the pull out force was defined as the Average pull out force minus three times the standard deviation. Sufficient Average and Minimum Expected pull out force is considered by the makers of flossing devices to be about 4 to more than five pounds.

TABLE 2

Pull out force for single-use flossing devices.

| Floss | n | Average (lbs) | Std. Dev. | Minimum Expected (lbs) |
|---|---|---|---|---|
| Unwaxed, 3 twists/inch | 20 | 10.18 | 1.34 | 6.17 |
| Waxed, 1.5 twists/inch | 28 | 7.33 | 2.17 | 0.82 |

Table 2 shows that both high twist, uncoated floss, and low twist, coated floss met the Average pull out force requirements. For the low twist, waxed floss, however, the Minimum Expected value of the pull-out force is less than one pound.

In a following example, the Insert Nozzle temperature was reduced from 315° C. to 255° C. to determine the effect of resin temperature on pull out strength.

EXAMPLE 3

The same mold and the same flosses were used as in Example 2. The first floss was an unwaxed UHMWPE DSM SK 65 yarn with 3 twists per inch. The second floss was UHMWPE DSM SK-65 400 denier, 1.5 twists per inch, 24.8 percent by weight of a coating composition containing 80 percent microcrystalline wax and 20 percent Honeywell EVA PE400. The production conditions were as follows:

Insertion Pressure: 500 lbs
Hold Pressure: 100 lbs
Barrel and manifold temperatures 182° C.
Insert Nozzle Temperature 255° C.
Cycle Time: 11.4 seconds The force to pull out the floss is shown on Table 3.

TABLE 3

Pull out force for single-use flossing devices.

| Floss | n | Average (lbs) | Std. Dev. | Minimum Expected |
|---|---|---|---|---|
| Unwaxed, 3 twists/inch | 20 | 10.68 | 1.03 | 7.59 |
| Waxed, 1.5 twists/inch | 28 | 9.12 | 1.29 | 5.25 |

Table 3 shows that both high twist, uncoated floss, and low twist, coated floss made under the noted conditions met the minimum pull out force requirements both for Average and Minimum Expected pull out force.

EXAMPLE 4

Example 3 was repeated except that the Insert Nozzle temperature was further reduced to 235° C. and then to 220° C. to determine the effect of resin temperature on pull out strength. The production conditions were as follows:

Insertion Pressure: 500 lbs
Hold Pressure: 100 lbs
Barrel and manifold temperatures 182° C.
Insert Nozzle Temperature 235° C. or 220° C.
Cycle Time: 11.4 seconds The force to pull out the floss is shown on Table 4.

TABLE 4

Pull out force versus insert nozzle temperature for single-use flossing devices.

| Insert Nozzle Temperature (° C.) | n | Average (lbs) | Std. Dev. | Minimum Expected (lbs) |
|---|---|---|---|---|
| 235 | 28 | 9.19 | 1.36 | 5.11 |
| 220 | 28 | 9.72 | 1.38 | 5.58 |

Table 4 shows that the low twist, coated floss made under the noted conditions met both the Average and Minimum Expected pull out force requirements.

EXAMPLE 5

This experiment shows the effect of using a heat sink on the pull out strength of single-use flossing devices. A mold was created similar to the mold used in Example 1. One side of the mold included grooves that were 0.800-inch wide and 0.002-inch deep, thus providing an aspect ratio of 40:1. Heat sinks similar to those shown in FIG. 1 were machined into the distal sections of the cavity in the other side of the mold halves such that, when the halves were brought together, the heat sinks were proximate the grooves and the length of floss positioned within the groove. The floss used was the same as that of Example 4 (DSM 400, 1.5 twists per inch) and had applied thereto 25.7 percent of a coating composition containing 80 percent microcrystalline wax and 20 percent Honeywell EVA. A similar floss holder was made using a mold having a groove with the same aspect ratio on one side, but without using a heat sink on the other side.

The production conditions were as follows:
Insertion Pressure: 500 lbs
Hold Pressure: 100 lbs
Barrel and manifold temperature 182° C.
Insert Nozzle Temperature 235° C.
Cycle Time: 11.4 seconds The force to pull out the floss is shown on Table 5.

TABLE 5

Pull out force with and without heat sink for single-use flossing devices.

| Heat sink | n | Average (lbs) | Std. Dev. | Minimum Expected (lbs) |
|---|---|---|---|---|
| Yes | 60 | 8.65 | 1.01 | 5.63 |
| No | 60 | 8.93 | 1.86 | 3.36 |

Table 5 shows that by utilizing a heat sink proximate the groove and the length of dental floss, the variation in the pull out force of the floss holder made in such a mold is reduced significantly, as evidenced by the reduction in the standard deviation by almost a factor of 2. In addition, the Minimum Expected pull out force was about 5.6 lbs, while the floss holder made in a mold without a heat sink was as low as 3.4 lbs. Thus, utilizing a heat sink in the lateral cavity portion of the mold synergistically provides both a robust process of manufacture and a floss holder with improved pull out, as evidenced by the reduction in standard deviation and the significant increase in Minimum Expected pull out force.

EXAMPLE 6

Since temperature of the entering resin has been shown to affect pullout force, experiments were conducted by changing the Insertion Nozzle temperature. The same molds were used as in Example 5. The floss used was the same as that of Example 4. The production conditions were as follows:

Insertion Pressure: 500 lbs

Hold Pressure: 100 lbs

Barrel and manifold temperature 182° C.

Insert Nozzle Temperature 220° C. or 270° C.

Cycle Time: 11.4 seconds

The force to pull out the floss is shown on Table 8.

TABLE 6

Pull out force versus insert nozzle temperature with and without heat sink for single-use flossing devices.

| Heat sink/Insert Nozzle Temperature (° C.) | n | Average (lbs) | Std. Dev. | Minimum Expected |
|---|---|---|---|---|
| Yes/220 | 28 | 9.71 | 0.80 | 7.31 |
| Yes/235 (Example 5) | 60 | 8.65 | 1.01 | 5.63 |
| Yes/270 | 28 | 8.15 | 1.16 | 4.68 |
| No/220 | 28 | 8.10 | 1.52 | 3.55 |
| No/235 (Example 5) | 60 | 8.93 | 1.86 | 3.36 |
| No/270 | 28 | 7.84 | 2.09 | 1.57 |

Table 6 again demonstrates that utilization of a mold that includes a heat sink in combination with a groove according to the present invention synergistically reduces product and process variation and significantly increases Minimum Expected pull out force at all injection nozzle temperatures. For the particular floss and process conditions used in this example, an insert nozzle temperature of about 220° C. yielded the optimum results, e.g. a Minimum Expected pull out force of about 7.3 lbs.

EXAMPLE 7

The same molds were used as in Example 5. The floss used was DSM 400, 1.5 twists per inch with a 26.6 percent coating of microcrystalline wax applied thereto. The production conditions were as follows:

Insertion Pressure: 500 lbs

Hold Pressure: 100 lbs

Barrel and manifold temperature 182° C.

Insert Nozzle Temperature 270° C.

Cycle Time: 11.4 seconds

The force to pull out the floss is shown on Table 9.

TABLE 7

Pull out force with and without heat sink for single-use flossing devices.

| Heat sink | N | Pull out force (lbs) | Std. Dev. | Minimum Expected |
|---|---|---|---|---|
| Yes | 56 | 8.31 | 1.03 | 5.21 |
| No | 56 | 9.05 | 1.44 | 4.75 |

Table 7 again demonstrates that utilization of a mold that includes a heat sink in combination with a groove according to the present invention synergistically reduces product and process variation and increases Minimum Expected pull out force.

EXAMPLE 8

Example 7 was repeated, but using highly twisted, uncoated floss. The same molds were used as in Example 7. The floss used was DSM 400, 3 twist per inch with no wax coating applied thereto. The production conditions were as follows:

Insertion Pressure: 500 lbs

Hold Pressure: 100 lbs

Barrel and manifold temperature 182° C.

Insert Nozzle Temperature 260° C.

Cycle Time: 11.4 seconds

The force to pull out the floss is shown on Table 8.

TABLE 8

Pull out force with and without heat s for single-use flossing devices.

| Heat sink | N | Average (lbs) | Std. Dev. | Minimum Expected (lbs) |
|---|---|---|---|---|
| Yes | 28 | 8.26 | 0.85 | 5.72 |
| No | 28 | 11.43 | 0.92 | 8.66 |

Table 8 shows that utilizing a mold that includes a heat sink when molding highly twisted, uncoated floss, actually reduces the Average and Minimum Expected pull out force, while having little effect on the variation (standard deviation) in the pull out force measurements. As such, it has been surprisingly discovered that by using a heat sink in the manufacture of single-use dental floss holders having wax coated floss, improvements in both process and product are exhibited, which is contrary to what one would expect.

EXAMPLE 9

A consumer test was conducted comparing the flossing device with the current floss (DSM 400 denier, Ultra High Molecular Weight Polyethylene SK-65, 3-twists per inch with no coating), shown as "Comparative" in Table 9, versus the same flossing device with a low twist coated floss (DSM 400 denier, Ultra High Molecular Weight Polyethylene SK-65, 1.5 twist per inch with a 26% coating of a composition containing 80 percent microcrystalline wax and 20 percent EVA, shown as "Invention" in Table 9.

TABLE 9

Average Consumer Rating of Products on a Scale of 1-10 (10 being highest) for a sample size (N) of 75.

| Attribute | Invention | Comparative | Confidence Limits |
|---|---|---|---|
| Overall Liking | 8.1 | 7.3 | 95% |
| Being easy to insert between teeth | 8.4 | 7.7 | 95% |
| Being easy to remove from between teeth | 8.3 | 7.5 | 95% |
| Not getting stuck between teeth | 8.2 | 7.4 | 90% |
| Being easy to slide between teeth | 8.3 | 7.7 | 90% |
| Being gentle on gums | 8.7 | 7.9 | 90% |
| Cleaning well between teeth | 8.6 | 8.0 | 90% |

The flossing device with the low twist wax coated floss was rated significantly better (at a 95% confidence limit) in Overall Liking, Being Easy to Insert between Teeth and Being Easy to Remove. The flossing device with the low twist floss was considered better (at a 90% confidence limit) on Not Getting Stuck between Teeth, Being Easy to Slide between Teeth, Being Gentle on Gums and Cleaning Well Between Teeth. On all other attributes, the products were rated equal, showing that that the Inventive floss holder exhibited no disadvantages versus the Comparative. This is significant in that it shows that flattening and coating the floss provided additional preferred benefits, without sacrificing any other properties, particularly with respect to fraying.

What is claimed is:

1. A mold for forming a single-use floss holder containing a length of dental floss comprising a wax composition applied thereto, said mold comprising:
 a first part comprising a first cavity disposed therein, said first cavity defined by a bottom base surface and a peripheral sidewall, said first cavity comprising,
  a base portion, and
  first and second spaced-apart portions having proximal and distal sections, said lateral portions extending from said base portion,
 a second part comprising a second cavity disposed therein, said second cavity defined by a bottom base surface and a peripheral sidewall, said second cavity comprising,
  a base portion, and
  first and second spaced-apart portions having proximal and distal sections, said later portions extending from said base portion and terminating in said distal section; and
 a groove having first and second terminal sections, a mid-section, and a substantially rectangular cross-sectional configuration, said groove extending an entire width of said second part, said first and second terminal sections of said groove traversing and coincident with said distal section of said first and second spaced-apart portions, respectively, said groove having an aspect ratio of about 10:1 or greater.

2. The mold of claim 1, wherein said groove has an aspect ratio of between about 10:1 and 100:1.

3. The mold of claim 1, wherein said groove has an aspect ratio between about 25:1 and about 75:1.

4. The mold of claim 1 further comprising a heat sink disposed proximate each of said first and second terminal sections of said groove.

5. The mold of claim 4, wherein said groove has an aspect ratio between about 25:1 and about 75:1.

6. The mold of claim 4 wherein said heat sink is disposed within said first part.

7. The mold of claim 4 wherein said heat sink is disposed within said second part.

8. The mold of claim 1 wherein said terminal section of said groove has a depth of about 0.002 inches.

9. The mold of claim 1 wherein said terminal section of said groove has a width of about 0.100 inches.

10. The mold of claim 1 wherein the width of said mid-section of said groove is greater than the width of said first and second terminal sections of said groove.

11. The mold of claim 1 wherein
 said base portion of said first cavity is substantially horizontal and comprises first and second terminal sections, and
 said first and second spaced-apart portions of said first cavity are substantially lateral, are substantially transverse to said base portion of said first cavity and extend from said first and second terminal sections of said base portion of said first cavity, respectively; and
 said base portion of said second cavity is substantially horizontal and comprises first and second terminal sections, and
 said first and second spaced-apart portions of said second cavity are substantially lateral, are substantially transverse to said base portion of said second cavity and extend from said first and second terminal sections of said base portion of said second cavity, respectively.

* * * * *